US007381557B2

(12) United States Patent
Mecsas et al.

(10) Patent No.: US 7,381,557 B2
(45) Date of Patent: Jun. 3, 2008

(54) COMPOSITIONS AND METHODS FOR BACTERIAL IMMUNITY AND SECRETION OF PROTEINS

(75) Inventors: Joan Mecsas, Needham, MA (US); Joan-Miquel Balada-Llasat, Malden, MA (US); Ralph Isberg, Newton Highlands, MA (US)

(73) Assignee: Tufts University, Boston, MA (US)

( * ) Notice: Subject to any disclaimer, the term of this patent is extended or adjusted under 35 U.S.C. 154(b) by 551 days.

(21) Appl. No.: 10/818,071

(22) Filed: Apr. 5, 2004

(65) Prior Publication Data

US 2005/0136075 A1 Jun. 23, 2005

Related U.S. Application Data

(60) Provisional application No. 60/460,887, filed on Apr. 7, 2003.

(51) Int. Cl.
*C12N 1/20* (2006.01)

(52) U.S. Cl. .................................................... 435/252.3

(58) Field of Classification Search .............. 435/252.3
See application file for complete search history.

(56) References Cited

U.S. PATENT DOCUMENTS 5,965,381 A 10/1999 Van Der Bruggen et al.
6,306,387 B1 10/2001 Galan
6,682,729 B1 * 1/2004 Powell et al. .............. 424/93.2
2002/0076417 A1 6/2002 Mahan et al.
2002/0077272 A1 6/2002 Mahan et al.

OTHER PUBLICATIONS

Michiels et al, Analysis of VirC, an operon involved in the secretion of yop proteins by *Yersinia entercolitica*, 1991, Journal of Bacteriology, vol. 173, pp. 4994.*
Stainer et al, YscP, a *Yersinia* protein required for yop secretion that is surface exposed, and released in low Ca2+, 2000, Molecular Microbiology, vol. 37, pp. 1005.*
Plano et al, Mutation in yscC, yscD, and yscG prevent high level expression and secretion of V antigen and yops in *Yersinia pestis*, 1995, Journal of Bacteriology, vo 177, p. 3843.*
Fukushima et al., Journal of Clinical Microbiology 29: 1271-1275, Jun. 1991.
Hueck, C.J., Microbiology and Molecular Biology Reviews 62: 379-433, Jun. 1998.
Igwe et al., Infection and Immununity 67: 5500-5507, Oct. 1999.
Julio et al., Infection and Immununity 69: 7610-7615, Dec. 2001.
Julio et al., Infection and Immununity 70: 1006-1009, Feb. 2002.
Mecsas et al., Infection and Immununity 67: 2779-2787, May 2001.
Sory et al., Microbial Pathogenesis 4: 431-442, 1988.
Sory et al., Infection and Immununity 60: 3830-3836, Sep. 1992.
Thornton et al., Vaccine 14: 977-981, 1996.

* cited by examiner

*Primary Examiner*—Mark Navarro
(74) *Attorney, Agent, or Firm*—Lawson & Weitzen, LLP; Sonia K. Guterman; Adam M. Schoen

(57) ABSTRACT

Attenuated strains of Gram negative bacteria carrying a mutation in one or more ysc genes or homologs are provided, as are methods of use for immunization against infection with a pathogenic strain and for delivery of a therapeutic agent.

21 Claims, 10 Drawing Sheets

Fig.2. *yscB-L*, *yscN-U* AND *yscB-U* PRODUCE YopM IN EQUAL LEVELS THAN WT *Y.pseudotuberculosis*, *yscB-UvirFG* ARE REDUCED. NONE OF THE MUTANTS SECRETES YopM
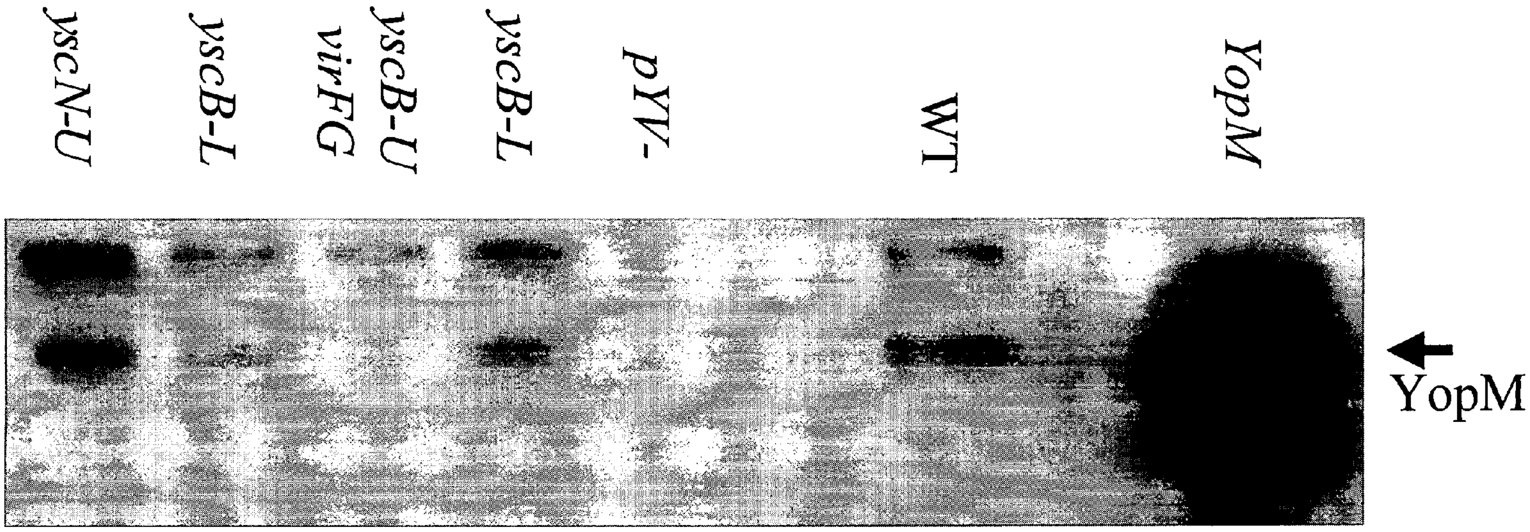
Lysates, 37°C, low $Ca^{2++}$ Fig.3. WT and *yscB-UvirFG Y.pseudotuberculosis* COLONIZATION IN THE BALB/C MOUSE MODEL
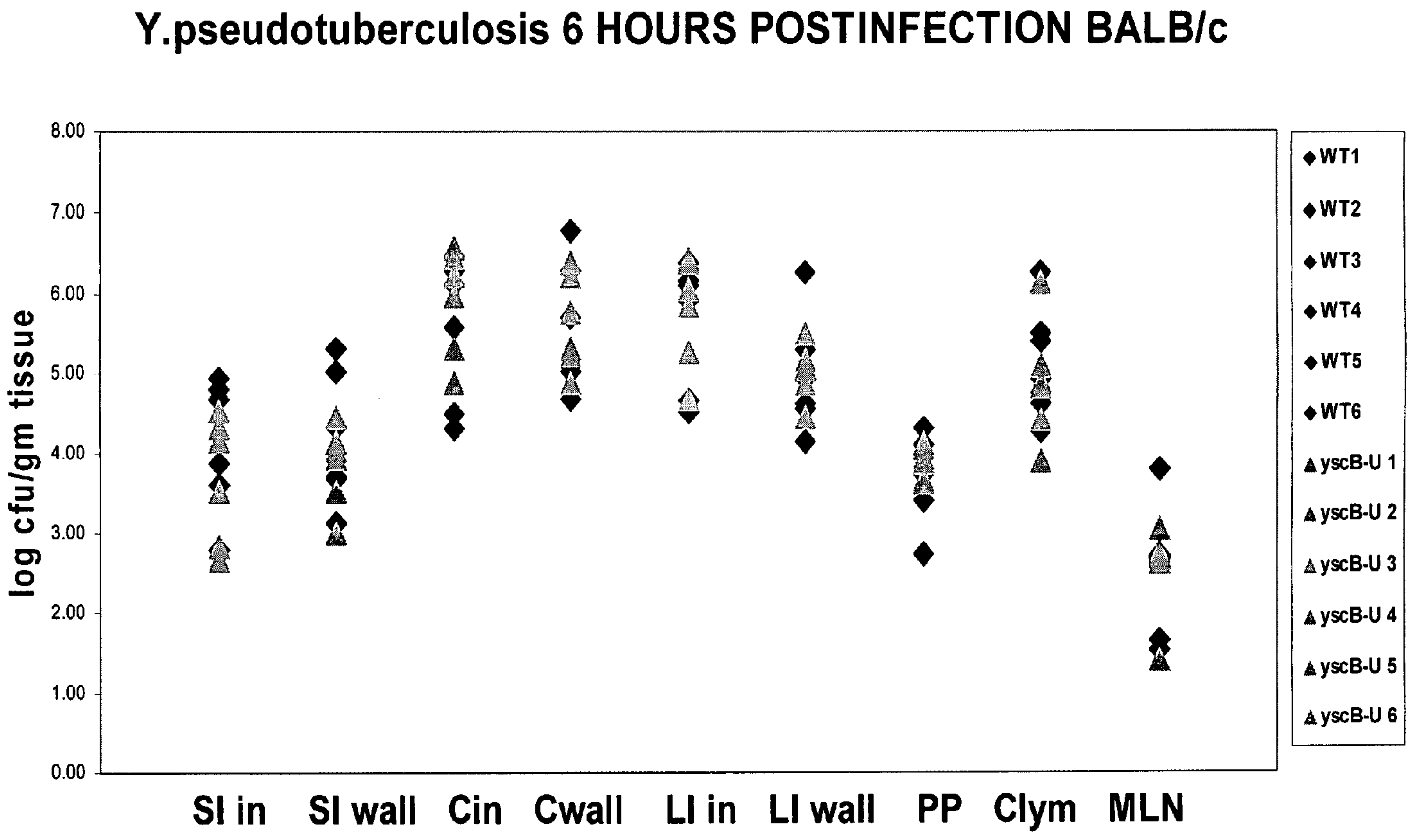

Fig.4. WT, *yscB-L*, *yscN-U*, *yscB-UvirFG* and pYV- *Y.pseudotuberculosis* COLONIZATION IN THE BALB/c MOUSE MODEL
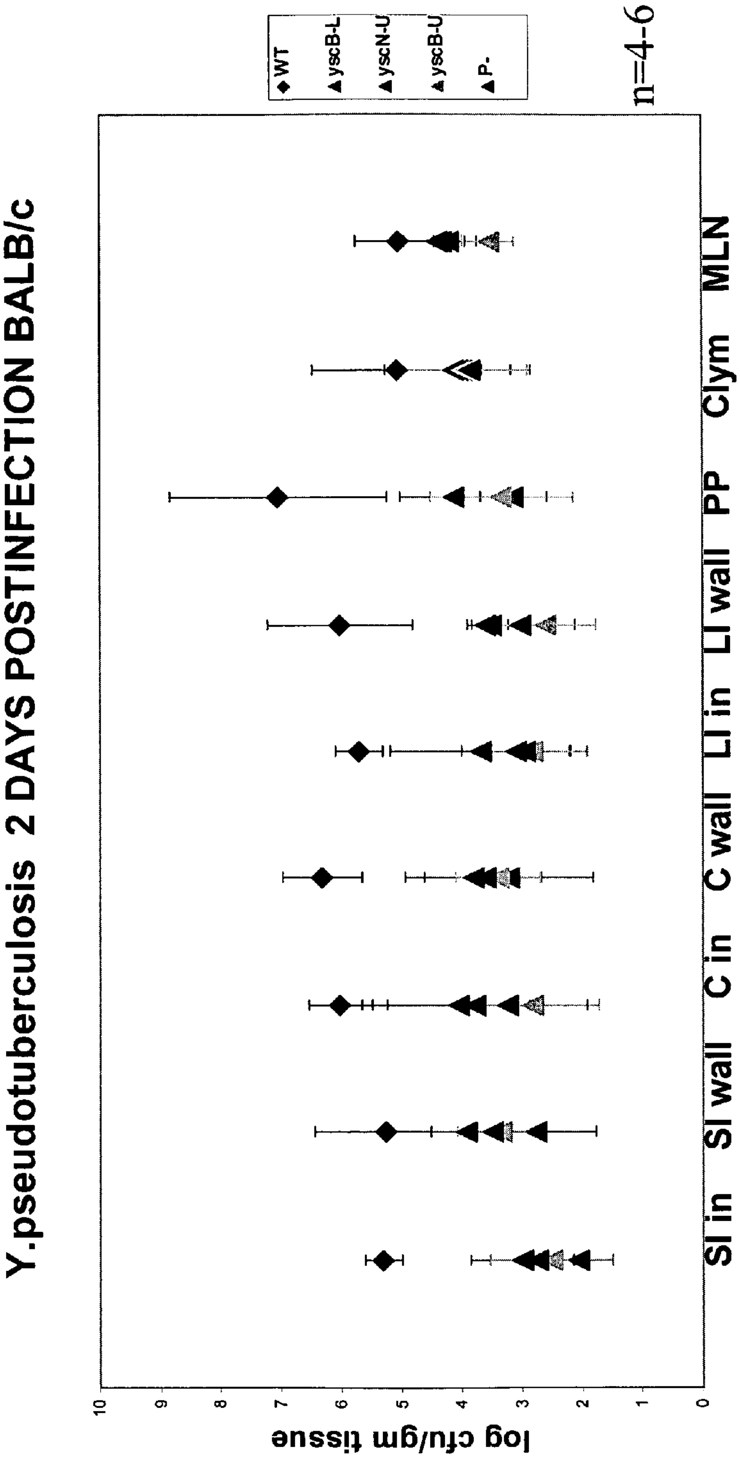

Fig.5. WT, *yscB-L*, *yscN-U*, *yscB-UvirFG* and pYV- *Y.pseudotuberculosis*
COLONIZATION IN THE BALB/c MOUSE MODEL
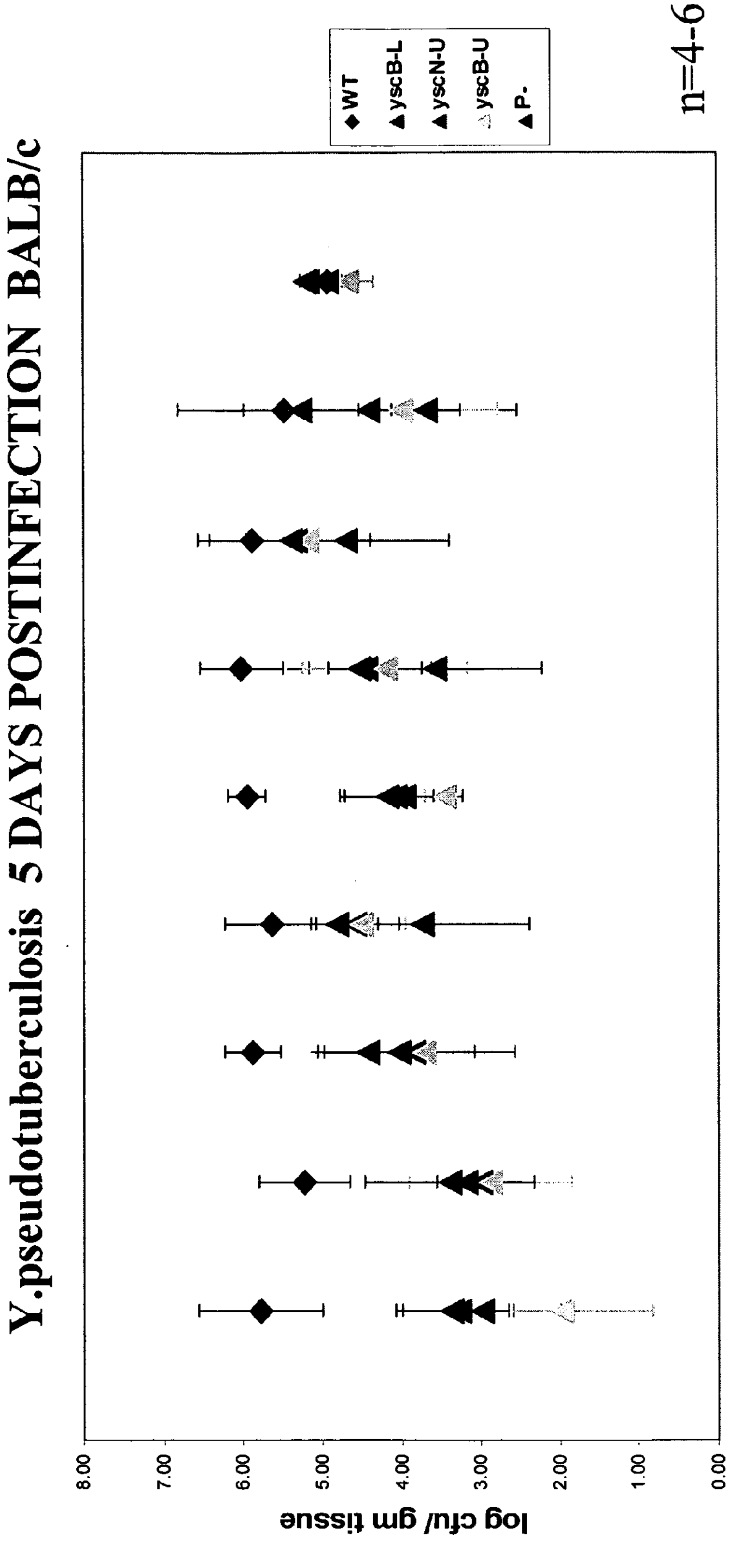

Fig.6. *E. coli* ISOLATED FROM BALB/c INTESTINAL FLORA COLONIZE THE MESENTERICLYMPH NODES AT 5 HOURS POSTINFECTION BUT IT IS ELIMINATED BY 2 DAYS
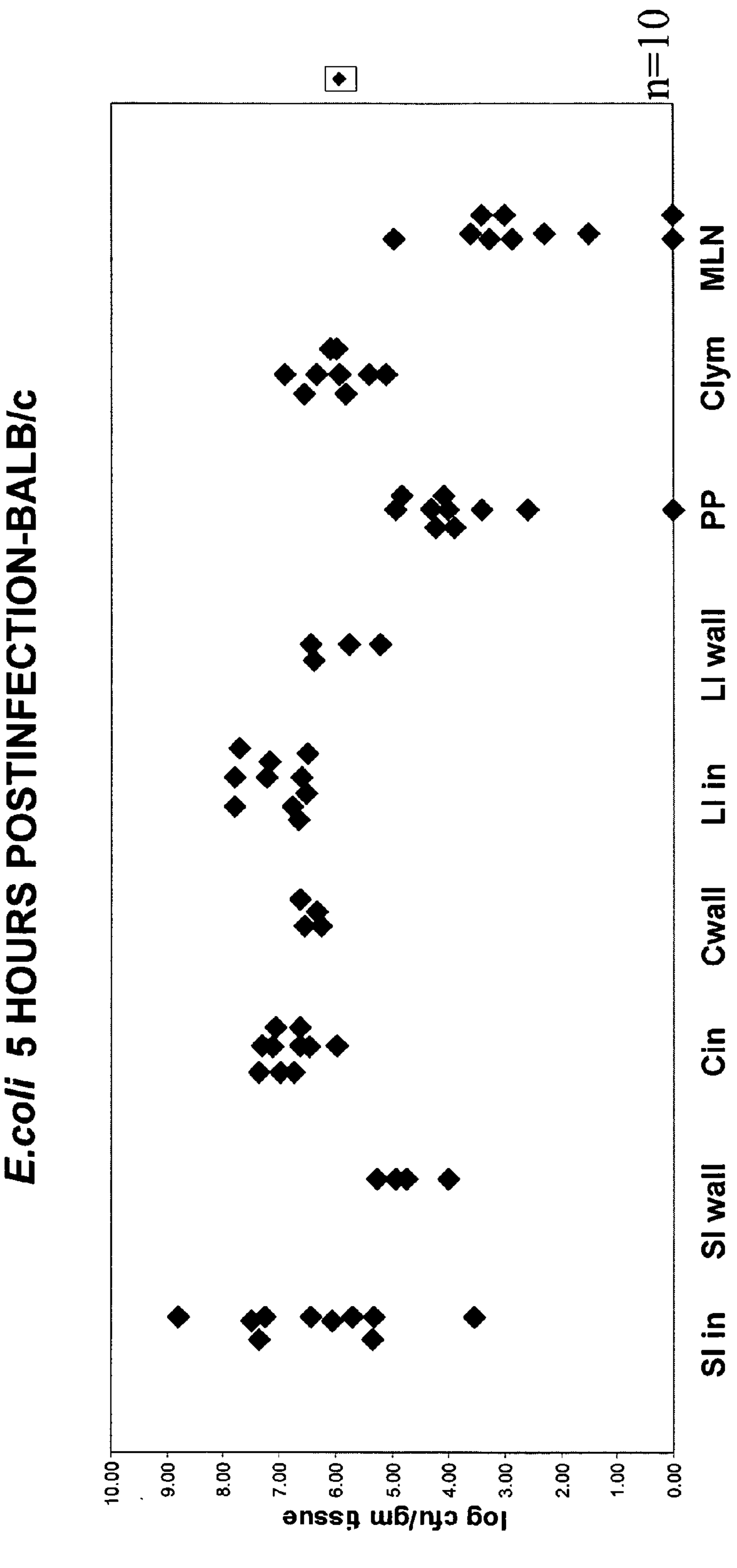

Fig.7. *E. coli* ISOLATED FROM BALB/c INTESTINAL FLORA COLONIZE THE MESENTERICLYMPH NODES AT 5 HOURS POSTINFECTION BUT IT IS ELIMINATED BY 2 DAYS
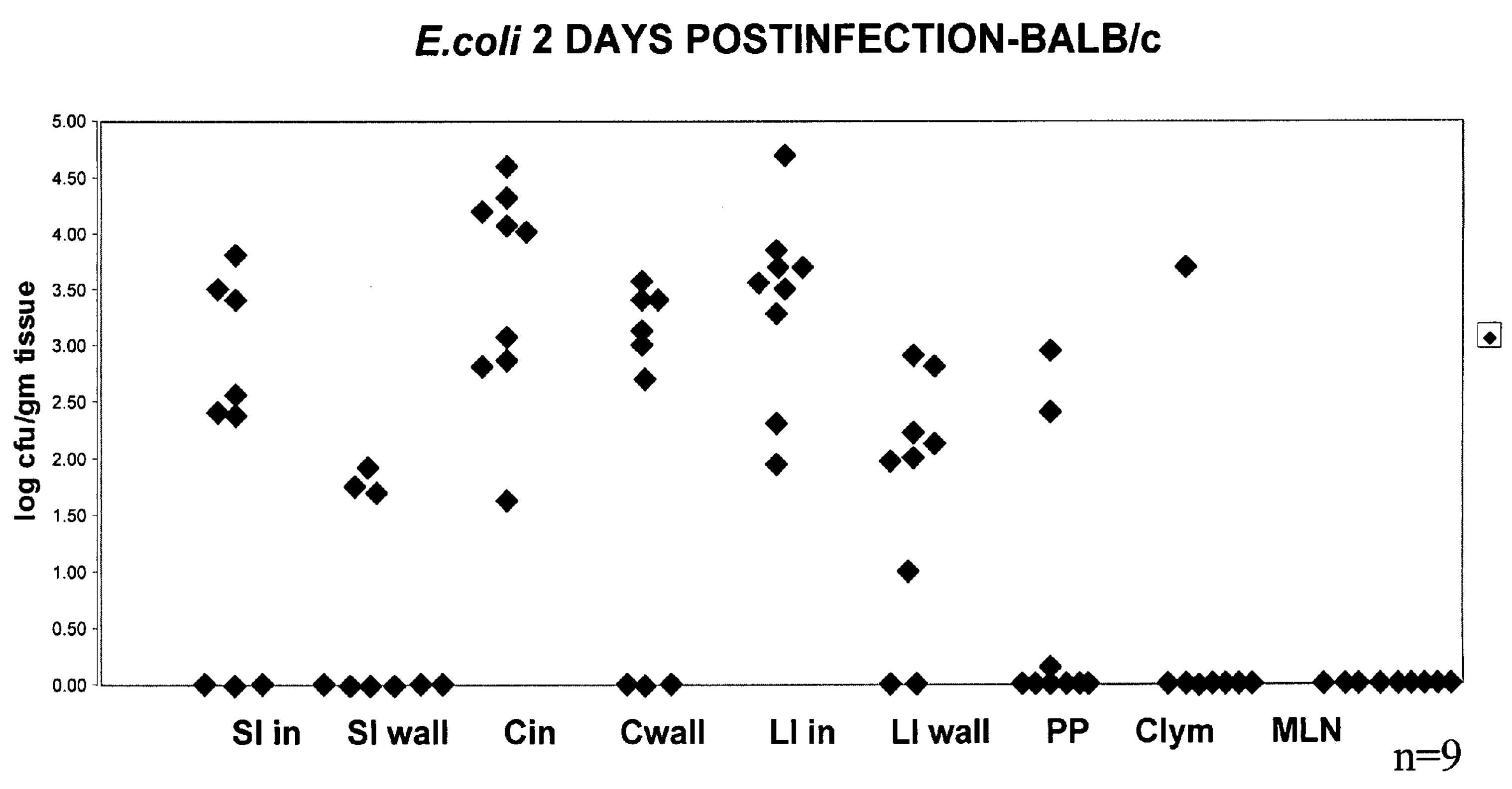

Fig.8. *Y. pseudotuberculosis* TYPE III SECRETION MUTANTS AND pYV-cured STRAINS CAN COLONIZE THE MESENTERIC LYMPH NODES OF C57BL/6J MICE
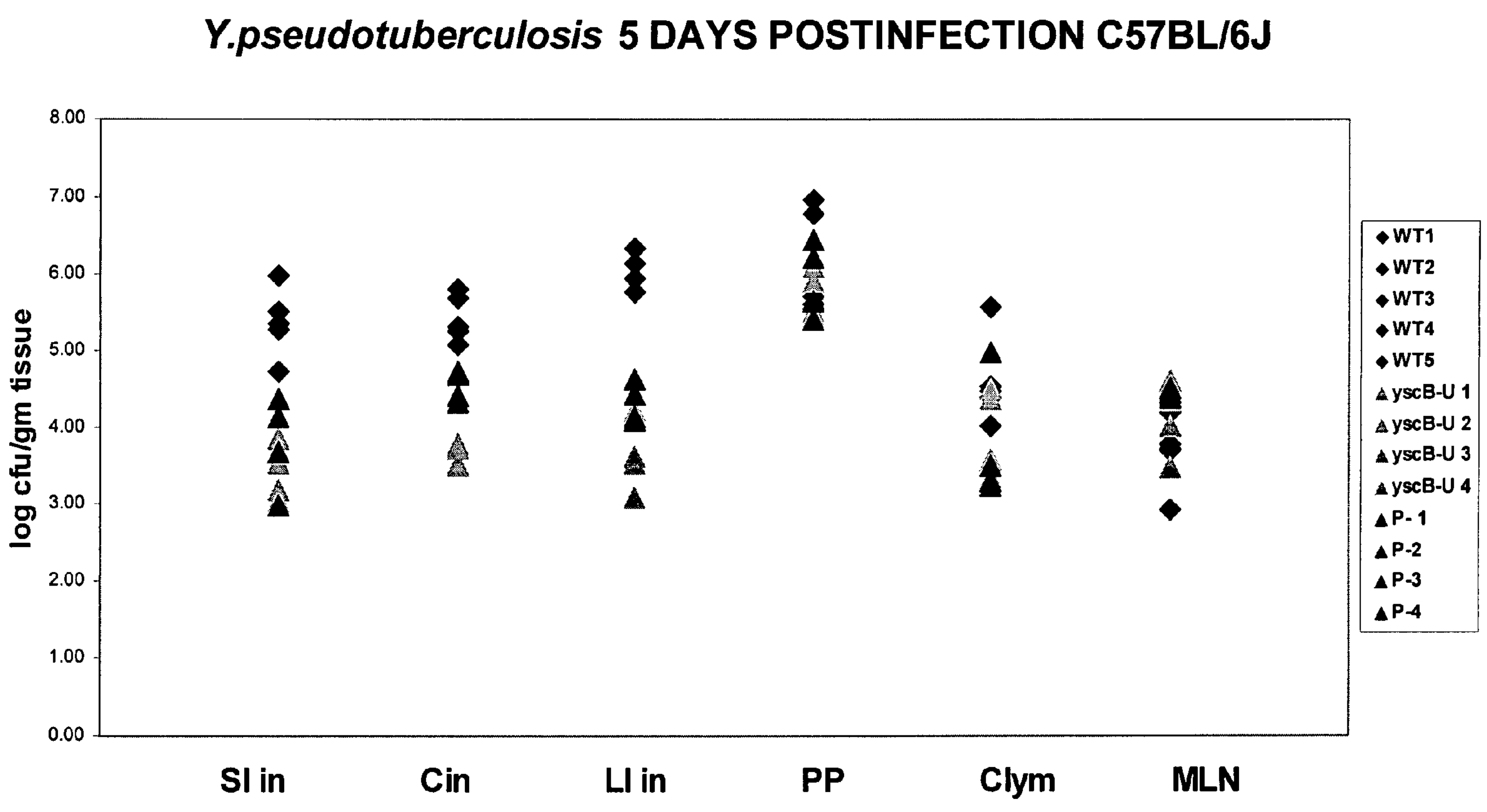

**Fig. 9. PLASMID-ENCODED TYPE III SECRETION MUTANTS PROTECT AGAINST *Y.pseudotuberculosis* VIRULENT STRAIN**
A - 1000 x LD50, primary infection
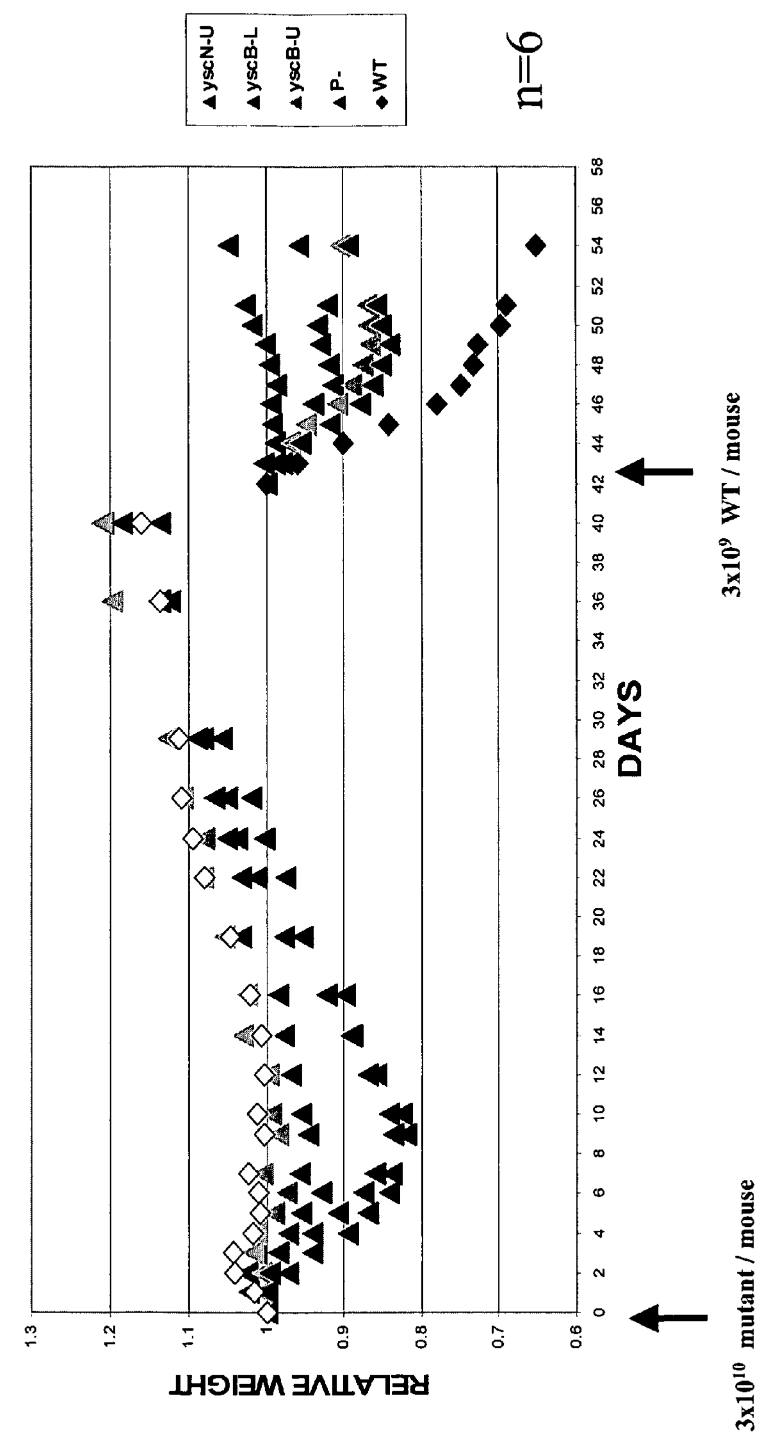

Fig.10. PLASMID-ENCODED TYPE III SECRETION MUTANTS PROTECT AGAINST *Y.pseudotuberculosis* VIRULENT STRAIN
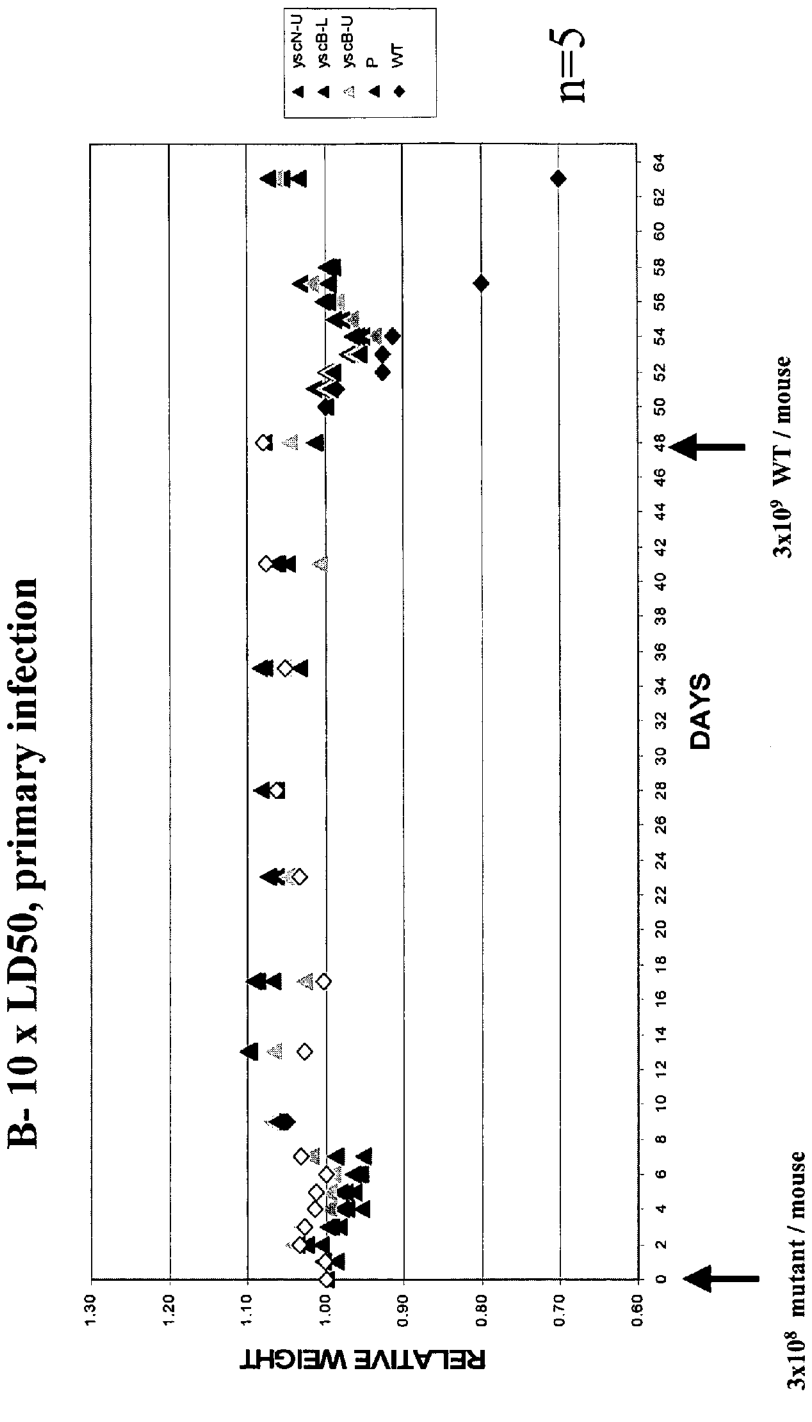

COMPOSITIONS AND METHODS FOR BACTERIAL IMMUNITY AND SECRETION OF PROTEINS

RELATED APPLICATION

This application claims the benefit of U.S. provisional application by Mecsas et al., having Ser. No. 60/460,887, filed Apr. 7, 2003 in the U.S. Patent and Trademark Office, and which is incorporated herein in its entirety by reference.

GOVERNMENT RIGHTS

This invention was made with with government support under grant number R21 AI49348 awarded by the National Institute of Allergy and Infectious Diseases of the National Institutes of Health. The government has certain rights in the invention.

TECHNICAL FIELD

The invention relates to attenuated strains of Gram-negative bacteria that carry a deletion of one or more genes in a class of genes involved in the apparatus for secretion of outer proteins, and methods for making and for use of these strains as vaccines against diseases such as plague, and as vectors for delivery of therapeutic agents.

BACKGROUND

*Yersinia pseudotuberculosis* is an enteropathogenic gram negative bacterial species that infects humans and other mammals. There are three species of *Yersinia* that are pathogenic for humans and other mammals: *Y. pseudotuberculosis* and *Y. enterocolitica* are enteric pathogens, and *Y. pestis* is the causative agent of bubonic plague and is believed to have evolved from *Y. pseudotuberculosis* less than 20,000 years ago. *Y pseudotuberculosis* is transmitted through the fecal-oral route, when contaminated food and water are ingested. Colonization requires the expression of one or more of the *Yersinia* virulence factors encoded in a naturally occurring plasmid, pYV.

The virulence plasmid pYV, found in pathogenic *Yersinia* strains, encodes about 30 genes that are responsible for encoding the structural, regulatory and secretory components of the type III secretion machinery, and for the effector molecules transported by this machinery called Yops (*Yersinia* outer proteins; see Hueck, C. J. Microbiol Mol Biol Rev 62: 379-433, 1998 for a review of type III secretion systems). This plasmid-encoded type III secretion system allows *Yersinia* to secrete and translocate Yops into the host cell where they disrupt cellular processes.

Chromosomal genes encoding a second type III secretion machinery have been found in *Yersinia* spps. The chromosomally-encoded type III secretion system in *Y. pseudotuberculosis* is different from the chromosomally-encoded type III secretion system found in *Y. enterocolitica*. In addition, a flagellar secretion system in *Y. enterocolitica, Y. pseudotuberculosis* and *Y. pestis* is a transport system that has homology to type III secretion systems.

SUMMARY

The present invention provides in one embodiment an attenuated strain of a *Yersinia* bacterial species, the bacteria comprising an altered ysc gene such that the bacteria are attenuated. The altered gene reduces secretion of *Yersinia* outer proteins (Yops); alternatively, the altered gene eliminates secretion of Yops; alternatively, the altered gene reduces synthesis of Yops. In one example of the embodiment, the bacteria are a species selected from the group of *Y. pseudotuberculosis, Y. pestis, Y. enterocolitica*, and *Y. ruckeri*. In general, the ysc gene has a deletion. A deletion mutation can not revert to wild type. The ysc gene deletion is selected from the group consisting of a deletion of: yscBL, yscNU, yscNU and virGF, and yscBL and yscNU. Further, the bacteria are in an effective dose.

The dose is effective to provide to a subject immunity against infection with a wild type *Yersinia*. The wild type *Yersinia* is selected from the group consisting of *Y. pseudotuberculosis, Y. pestis, Y. ruckeri*, and *Y. enterocolitica*. The effective dose provides immunity to at least about two orders of magnitude more wild type *Yersinia* bacterial cells than a level of immunity in a non-immunized subject. More specifically, the effective dose provides immunity to at least about three orders of magnitude more wild type *Yersinia* bacteria compared to a level of immunity in a non-immunized subject; the effective dose provides immunity to at least about four orders of magnitude more wild type *Yersinia* bacteria compared to a level of immunity in a non-immunized subject. The effective dose comprises for example, about $10^4$ to about $10^8$ bacteria per kg body weight of the subject. Alternatively, the effective dose comprises about $10^8$ to about $10^{12}$ bacteria per kg body weight of the subject. The attenuated strain in certain embodiments further comprises a mutation to kasugamycin resistance.

The subject is a vertebrate animal, for example, the subject is selected from the group of a mammal, a fish, and a bird. The immunity can be conferred on mammalian subjects that are humans, and on non-human mammal subjects that are agriculturally important such as cows, horses, goats, sheep and pigs, on mammals that are subjects involved in experimental trials such as rodents such as mice, rats, guinea pigs, or rabbits, or zoo animals such as pandas, zebras and giraffes, and on non-mammal animal subjects such as fish, for example, fish involved in aquaculture such as salmon and trout.

In another embodiment, administering the attenuated strain to the subject, for example, to a mammal, provides bacteria that persist in mesenteric lymph nodes of the mammal. The strain in a further embodiment also comprises a recombinant gene. The recombinant gene encodes a desired gene product, for example, the gene product is selected from the group consisting of an interferon, an erythropoietin, an enzyme, a growth factor, a leukokine, a chemokine, an antigen, a peptide hormone, and a precursor of any of these.

Also provided herein is an attenuated strain of a Gram-negative bacteria, the strain comprising an altered ysc-like gene such that the bacteria are attenuated. For example, the attenuated strain can have an altered gene of a *Salmonella* species selected from the group of spa, spi, inv, and ssa genes. The species is selected from the group of *S. typhi, S. typhimurium, S. minnesota, S. gallinarum* and *S. pullorum*. Alternatively, the altered gene is a gene of a *Shigella* species, and the gene is selected from the group of spa and mxi genes. The *Shigella* is selected from the group of: *S. dysenteriae, S. boydi, S. flexneri*, and *S. sonnei*. Alternatively, the altered gene is a gene of an *Escherichia* species, and the gene is selected from the group of ssc, sep and esc genes. For example, the strain is selected from the group of an enterotoxigenic strain (ETEC), an enteropathogenic (EPEC) strain, an enterohemorrhagic (EHEC) strain, a venous thromboses-producing (VTEC) strain, and an enteroinvasive (EIEC)

strain. Alternatively, the altered gene is an altered psc gene of a *Pseudomonas* species. The *Pseudomonas* is selected from the group of *P. aeruginosa* and *P. fluorescens*. Alternatively, the altered gene is an altered bsc gene of a *Bordetella* species. The *Bordetella* is selected from the group of *B. avium, B. pertussis, B. bronchiseptica*, and *B. parapertussis*. Alternatively, the altered gene is an altered bsc or cds gene of a *Chlamydia* species. The *Chlamydia* is selected from the group of *C. psittaci, C. trachomatis*, and *C. pneumoniae*. Alternatively, the altered gene is an altered bsc gene of a *Vibrio* species. The *Vibrio* species is selected from the group of *V. cholerae, V. cholerae* O1, *V. cholerae* non-O1, *V. vulnificus*, and *V. parahaemolyticus*. Alternatively, the strain is a pathogenic strain selected from the group of: *Y. pseudotuberculosis, Y. pestis, Y. ruckeri, Y. enterocolitica, E. coli* O157:H7, *Shigella dysenteriae, Salmonella typhi, Salmonella minnesota, Salmonella paratyphi, Salmonella typhimurium, Pseudomonas aeruginosa, Vibrio cholera, Chlamydia trachomatis, Chlamydia pneumoniae, Bordetella pertussis, B. bronchiseptica*, and *Burkholderia* cepacia.

The aforementioned Gram-negative bacterial strains are pathogenic for various vertebrate animal subjects, including warm blooded animals such as birds and mammals, including humans. In addition, type III secretion systems are known in Gram negative bacterial strains that are pathogenic for plants, including plant pathogenic species *Erwinia amylovora, E. carotovora, Xanthomonas campestris*, and *Pseudomonas syringae*. Embodiments of the attenuated Gram negative bacterial strains of the present invention include plant pathogens. Attenuated plant pathogenic bacterial strains can be applied to crop plants to occlude growth and spoilage of the crops by wild-type strains of bacteria. As with pathogenic bacteria that infect animal subjects, the attenuated strains of the plant pathogenic bacteria can be further attenuated by additionally comprising a mutation to kasugamycin resistance.

Another embodiment of the invention provided herein is a method of providing immunity from infection by a wild type *Yersinia* to a subject, the method comprising administering to the subject an effective dose of an attenuated strain of *Yersinia* comprising an altered ysc gene, wherein the dose confers immunity on the subject to a disease state caused by the wild type *Yersinia* bacteria. In an exemplary embodiment, the subject is a human. Alternatively, the subject is selected from the group of a farm animal, a ranch animal, a zoo animal, a laboratory animal, a companion animal, and a wild animal. Further, the disease is bubonic plague, pneumonic plague, enterocolitis, colitis, pneumonia, or pseudotuberculosis.

Another embodiment of the invention provided herein is a method of reducing frequency of incidence of plague in a human population contiguous to an animal population reservoir, the method comprising administering to the animal population an attenuated *Yersinia* strain having an altered ysc gene. For example, the animal is a rodent, for example, the animal is a rat. In an exemplary embodiment, a method is provided of reducing frequency of incidence of plague in a human population contiguous to an animal reservoir such as a rat population, the method comprising administering to the rat population an attenuated *Yersinia* strain having an altered ysc gene.

A method is provided of delivering a peptide drug to a subject comprising administering to the subject an attenuated strain of *Yersinia* comprising an altered ysc gene and carrying a recombinant gene encoding the drug. The subject is selected from the group consisting of a human, a sheep, a goat, a cow, a rabbit, a horse, a dog, a cat, a gorilla, a chimpanzee, a rat, a mouse, a chicken, a turkey, a duck, and a goose. In various embodiments, the subject is a farm animal, a zoo animal, a ranch animal, an aquaculture animal, a companion animal, a laboratory animal, or a human. In various embodiments, the subject is a vertebrate animal such as a reptile, for example, a lizard, turtle, or snake; the subject is a bird such as a chicken, turkey, condor, or crane; or the subject is a mammal such as a primate, an ungulate, a rodent, a carnivore, and a pachyderm. In another embodiment, the subject is a crop plant such as a vegetable or a fruit crop.

Another embodiment of the invention provided herein is a method of making a vaccine for immunizing a subject population against infection by a Gram-negative bacterial pathogen, the method comprising providing an attenuated Gram-negative bacterial strain having an altered ysc-like gene in a pharmaceutically acceptable carrier. Yet another embodiment of the invention provided herein is a method of making a vaccine for delivering to a subject a desired therapeutic agent, the method comprising providing an attenuated Gram-negative bacterial strain having an altered ysc-like gene and a recombinant gene encoding the agent, in a pharmaceutically acceptable carrier.

Another embodiment of the invention provided herein is a method of protecting a crop plant from infection by a pathogenic Gram negative bacterial species, the method comprising spraying the plant with an attenuated strain of the species lacking a ysc-like gene. The species is selected from the group of plant pathogens *Erwinia carotovora, E. amylovora, Xanthomonas campestris*, and *Pseudomonas syringae*.

The present invention in another embodiment provides a kit for immunizing a subject against infection by a Gram negative bacteria having a ysc-like gene, the kit comprising at least one unit dose of an attenuated strain of the Gram negative bacteria having an altered ysc-like gene. For example, the unit dose is an effective dose to provide immunization against infection by a wild type strain. Alternatively, the bacteria further comprise a heterologous recombinant gene encoding a desired gene product, and the unit dose is an effective dose for providing the desired gene product to the subject. The kit can further comprise any of a container, a pharmaceutically acceptable carrier, and instructions for use.

BRIEF DESCRIPTION OF THE DRAWINGS

FIG. 2 is a photograph of an SDS-PAGE electrophoretogram showing production of Yop M protein by the deletion mutant cells s in comparison to wild type (WT) cells of *Y. pseudotuberculosis*.

FIG. 3 is a graph showing the log of number of bacteria/gram of various tissues of either WT or yscB-U deletion strains of *Y. pseudotuberculosis*, at 6 hours after infection, in mice of strain BALB/c. Abbreviations used in the Fig. for various organs are as follows: mesenteric lymph nodes (MLN), Peyer's patches (PP), cecal lymph node (Clym), cecal lumen (Cin), cecal wall (Cwall), ileum (small intestine) lumen (SI in), ileal wall (SI wall), colonic (large intestine) lumen (LI in) and colonic walls (LI wall).

FIG. 4 is a graph as in FIG. 3, at 2 days after infection, of either WT or four different deletion mutants.

FIG. 5 is a graph as in FIG. 4, at 5 days following infection. At this time point, the only tissue having mutant bacteria at a level comparable to WT is mesenteric lymph node (MLN).

FIG. 6 is a graph as in FIGS. 3-5, however using an *E. coli* strain isolated from mouse intestine. Data indicate that bacteria in the MLN are present in tissues at 5 hours following infection.

FIG. 7 is a graph as in FIG. 6, showing that *E. coli* cells at 2 days after infection are entirely eliminated from MLN.

FIG. 8 is a graph showing number of bacteria per gram in various tissues following infection by various WT or mutant *Y. pseudotuberculosis* strains in mice of strain C57B1/6J. Similar data are found here as were obtained in BALB/c mice, FIG. 3.

FIG. 9 is a graph of weight of animals during a time course of immunization, showing that a high dose (1000-fold greater than the LD50) infection with various mutant *Y. pseudotuberculosis* strains, but not WT, protects against subsequent infection at day 42 with WT bacteria.

FIG. 10 is a graph as in FIG. 9, further showing that a lose dose (10-fold greater than the $LD_{50}$) infection is also protective, and less deleterious to the animals.

DESCRIPTION OF EMBODIMENTS

Figure 1:
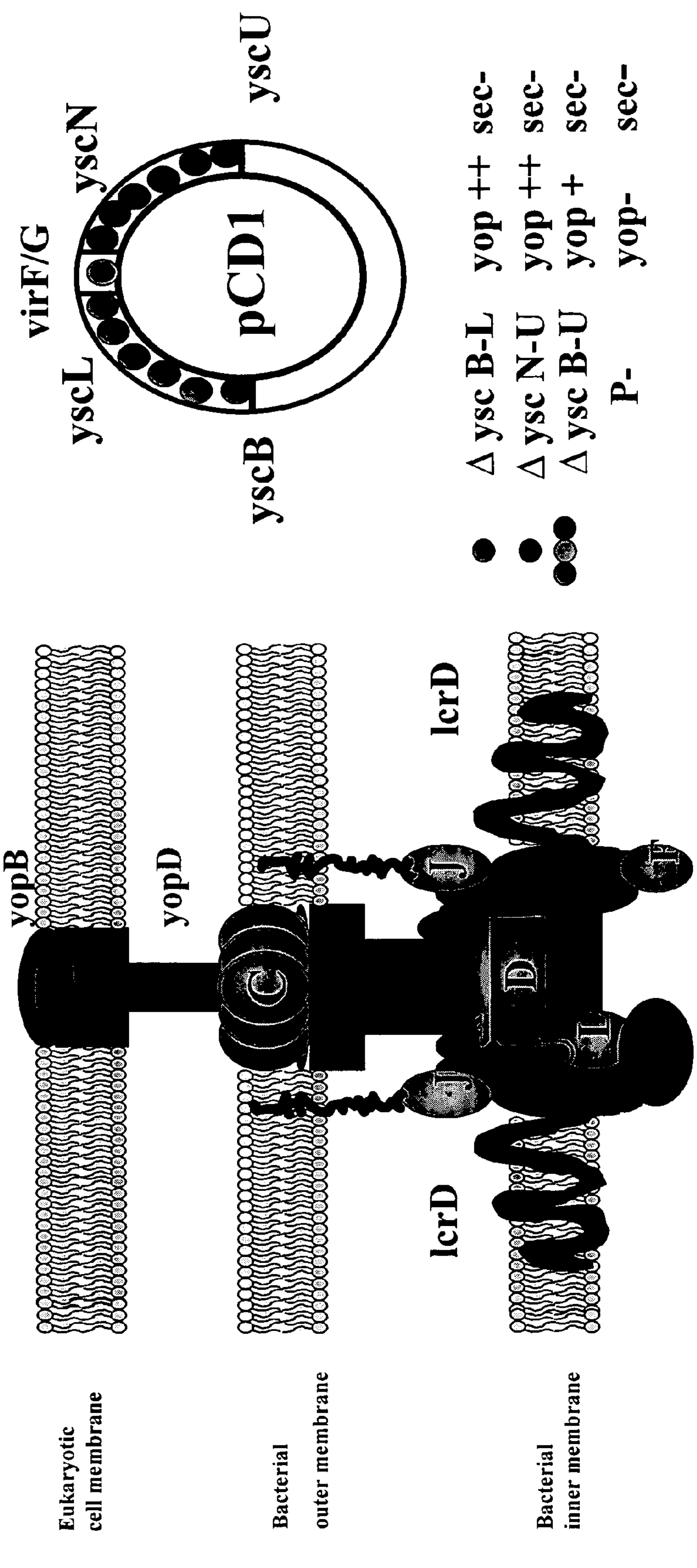
FIG. 1 is a diagram showing components of a *Yersinia* secretion system and their location in bacterial inner and outer membranes and the eukaryotic cell membrane, on the left, and showing a plasmid having ysc genes and the effect of deletions of these genes on expression and secretion of Yop, on the right.

Previous live attenuated *Y. pseudotuberculosis* strains have been described as potential candidates for vaccines. These strains were shown to colonize the mesenteric lymph nodes (MLN) poorly at day 5 (Julio et al. Infect Immun. 69: 7610-15, 2001); Julio et al, Infect Immun. 1006-1009, 2002) and thus may not be present long enough for the host to generate a strong immune response to heterologously expressed antigens and/or other *Yersinia* strains. Other potential *Y. pseudotuberculosis* vaccine strains require over-expression of an enzyme (Julio et al. Infect Immun. 70: 1006-9, 2002); Julio et al, 2001. Infect. Immun. 7610-7615), a property which may be unstable or revert back to the original phenotype during the course of an infection. Alteration of the native level or activity of the enzyme DNA methylase (Dam) inhibits virulence of the bacteria (see also U.S. patent applications 2002/0077272A1 and 2002/0076417A1).

As *Y. pseudotuberculosis* is very closely related to *Y. pestis*, it is a desirable strain to use as a starting point for development of a vaccine. Strains of the species *Y. pseudotuberculosis* ysc which are deletion mutants are surprisingly found herein to be attenuated and to confer immunity to infection with *Y. pestis*, and hence these strains can provide a vaccine against bubonic plague. A live oral attenuated *Y. enterocolitica* strain was described as a vaccine (Igwe et al. Infect Immune 67: 5500-5507 (1999), however this species may not share a sufficient number of epitopes with *Y. pestis* to protect recipient animals from subsequent infection. Other strains of *Y. pseudotuberculosis* which have been reported to confer immunity have not been characterized genetically (Thornton and Smith, Vaccine 14: 997-981, 1996).

Delivery of proteins to eukaryotic cells by recombinant *Yersinia* mutant strains defective in one or more yop genes has been shown (U.S. Pat. No. 5,965,381) In these strains, a YopE signal sequence termed "effector protein" is used to direct secretion of a heterologous protein which is fused in frame to the 3' end to the sequence. A Gram negative bacterium *Salmonella typhimurium* strain having a type III section system promoter linked to a protein of interest or an immunogenic portion thereof is shown in U.S. Pat. No. 6,306,387,387 B1 .

As used herein and in the claims, the following terms shall have the following meanings unless the context otherwise requires.

A "deletion" as is well known in the art of genetics is a mutation having loss of at least one nucleotide as the molecular basis of the change in the mutant gene. A deletion preferably has a loss of a plurality of nucleotides.

"Secretion" of a protein as it is well known in the art of cell biology is a process by which a protein is transported across a membrane. Generally, the process is facilitated by the protein having a short amino acid sequence located, for example, at the amino terminal of the protein, known as a "leader" sequence or a "secretion signal" sequence. The term "synthesis" of a protein refers to the in vivo process of translation of mRNA encoding the protein into an amino acid polymer or polypeptide. The terms protein and polypeptide shall have the same meaning.

The term "pharmaceutically acceptable carrier" includes any and all solvents, dispersion media, coatings, antimicrobials such as antifungal agents, isotonic and absorption delaying agents and the like that are physiologically compatible and that are not harmful to the attenuated bacteria of the composition. Preferably, the carrier is suitable for oral, intravenous, intramuscular, intraperitoneal, or subcutaneous administration, and the active component which is the bacteria can be coated in a material to protect it from inactivation by the action of acids or other adverse natural conditions. Compositions in particular preparations can include agents to stabilize the bacteria to freezing, such as glycerol or dimethyl sulfoxide (DMSO). As is known to one of ordinary skill in the bacteriological arts, the attenuated strains can be preserved for long term storage by freezing, for example at −20C or −70C, or by freeze drying or lyophilization.

The term "immunity" is defined by the results of the examples presented herein, and refers to a status of an animal subject that has previously survived an infection by an immunizing organism, such that a subsequent infection is characterized by less severe symptoms and a lower incidence of death in comparison to a "naïve" animal that has not been so previously infected. The initial infection is the "primary" infection, and the subsequent infection is the "secondary" infection or challenge. In the examples presented herein, the primary immunizing infection is accomplished using an effective dose of an attenuated strain of a Gram negative bacterium having an altered ysc-like gene, such as a *Yersinia* strain having a ysc deletion. The subsequent secondary infection or challenge is achieved using a wild type strain (WT) with fully functional ysc genes.

A "ysc-like" gene means a gene that is part of a type III secretion system of a Gram negative bacterial strain, genus or species, such that a mutation in the gene causes a reduction in synthesis or secretion of an outer protein, commonly referred to as "effector proteins" or an "effector molecule". The exemplary group of genes, termed ysc in various species of the bacterial genus *Yersinia*, are substantially identical in nucleotide sequence to genes of comparable function in numerous other Gram negative genera. In one embodiment, a ysc-like gene is at least about 20% identical, at least about 30% identical, at least about 40% identical, at least about 50% identical, or at least about 70% identical in amino acid sequence to a ysc gene of a *Yersinia* species (Hueck, C. J., Micro Mol Bio Rev 62: 379-433, 1998, the entire contents of which are incorporated herein by reference). The ysc genes are named for *Yersinia* secretion and bear a variety of other names in other Gram negative bacteria, such that a unified nomenclature for ysc-like proteins, sct (for secretion and cellular translocation) has been proposed (Hueck, 1998). As used herein, the designation "ysc-like" to refer to genes and their encoded proteins in the Gram negative bacteria, and the designation "sct" shall have the same meaning.

The roles of the two type III secretion systems in the ability of *Y. pseudotuberculosis* to colonize different tissues in mice were initially investigated as described herein to elucidate a variety of data, including identifying the tissues in which function of the pYV-encoded system is necessary for bacterial colonization, is necessary for function of the chromosomally-encoded type III secretion system both in an animal infection and/or in a test tube to transport the Yops in the absence of the plasmid encoded system, and for the role of the chromosomally-encoded system for tissue colonization in mice.

In order to investigate if the plasmid-encoded type III secretion system is important for colonization of the gastrointestinal system, four mutant strains were generated. Strains yscBL and yscNU lack operons that encode the structural components of the type III secretion system, and retain the genes for the yops and the positive regulator, virF, of the Yops. Strains having a genotype yscBUvirFG lack both the structural components and a positive regulator of the Yops; and strain P-, lacks the pYV plasmid (see FIG. 1). Surprisingly, these strains were found to be attenuated, and to confer immunity to animals that had been treated with these mutant cells prior to infection with a wild-type pathogen. These strains were constructed by standard recombinant techniques, such as are known to one of ordinary skill in the art of molecular biology.

The attenuated Gram negative bacterial strains, or the attenuated and recombinant Gram negative bacterial strains exemplified by the *Yersinia* ysc mutants of the present invention are employed herein in vivo, and efficacy at high and low doses have been established. An "effective dose" is an amount of the composition that remediates either or both of clinical symptoms associated with a secondary infection, and frequency of death of individuals in an infected population.

Further in vivo use of these and other strains provided herein can be tested for safety in animals. In this case, the strains may be administered to the animal orally or directly into the stomach. The animals may be sacrificed after a few days (for example, 1 to 3 days) after administration of the bacteria. For analysis, the intestines of sacrificed animals are washed and the Peyer patches or the faeces can be examined for viable bacterial cells. See, e.g., Sory et al. (1992) Infect. Immun. 60: 3830-3836.

The attenuated Gram negative bacterial strains, or the attenuated and recombinant Gram negative bacterial strains such as the *Yersinia* ysc mutants may also be administered to the animal by intraperitoneal injection. Organs of sacrificed animals such as spleen and liver can be examined for the presence of intracellular bacteria, an indication of insufficient safety. Intracellular bacteria may be detected by e.g., cultivating cell extracts by inoculating samples of the extracts onto solid medium. See Sory et al. (1988) Microb. Pathogen 4: 431-442.

A safe recombinant attenuated Gram negative strain may be employed in an immunogenic composition to induce an immune response for treating various pathological conditions in mammals. The pathological conditions contemplated by the present invention include tumors and infections by pathogenic organisms, as disclosed herein. The immunogenic compositions can include, in addition to a recombinant Gram negative bacteria, other substances such as cytokines, adjuvants and pharmaceutically acceptable carriers. Cytokines can also be included in such immunogenic compositions using additional recombinant bacteria of the present invention capable of delivering a cytokine, for example. These immunogenic compositions may be administered to the subject in any convenient manner, such as orally, intraperitoneally, intravenously or subcutaneously. Specific immune responses induced by such compositions can lead to CTL-mediated or antibody-mediated killing of the pathogens or cells having the presence of or the abnormal expression of a relevant antigen, thus alleviating the relevant pathological condition.

The present invention is further illustrated by the following examples, which are exemplary only and are not meant to be further limiting. All the publications mentioned in the present disclosure are incorporated herein by reference in their entirety. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

EXAMPLE 1

Construction of ysc Mutant Strains of *Y. Pseudotuberculosis*

To generate deletions of the ysc operons, PCR primers were designed to amplify approximately 400 base pairs of each of genes yscN, yscU, yscB, and yscL. The 400 base pair DNA products from yscB and yscL, yscN and ysc U, and yscN and yscL were ligated into pCVD422 at the SalI, SphI sites and SphI and SacI sites, resulting in three plasmids identified herein as pJMBL1, pJMBL2 and pJMBL3. Each of the plasmids pJMBL1, pJMBL2 and pJMBL3 were electroporated into cells of *E. coli* strain SM10λpir and the resulting strains obtained were mated with *Yersinia pseudotuberculosis*. Cell culture was performed using conditions of temperature (26C or room temperature) and media (LB broth or 2xYT broth) that are standard for this organism.

Irgasan-ampicillin-resistant colonies were selected, and the Irgasan-ampicillin-resistant clones obtained were colony purified and grown in LB broth at 26C without drugs for 16 hours. The bacteria were plated on L plates containing 10% sucrose. Colonies were patched onto LB plates, LB plates containing Conga Red and LB plates containing ampicillin. Colonies that were white on Conga Red plates and were ampillicin-sensitive were further screened by PCR for the presence of other genes on pYV, including yopE, yopH and yopM. Clones containing other genes on the virulence plasmid, and lacking the ysc operons were used for in vitro, cell culture and animal studies.

The plasmids pJMBL1, pJMBL2 and pJMBL3 were used to generate deletions of ysc operons in *Y. pestis* and ampicillin-sensitive strains of *Y. enterocolitica*. A map of a portion of pYV is shown below:

| | | | | | | | |
|---|---|---|---|---|---|---|---|
| tyeA yopN | yscN.O.P.Q.R..S.T..U | virG..F | yscA | yscB..C..D..E..F..G..H..I..J..K..L..M | lcrS | | |
| PCR products: | | | | | | | |
| yscN | yscU | | yscB | | yscL | | |
| SalI_SphI | SphI_SacI | | SalI_SphI | | SphI_SacI | | |

The plasmids constructed are: pJMBL1 has yscN and yscU fragments cloned into the SalI, SphI and SacI sites of pCVD442; pJMBL2 has yscB and yscU fragments cloned into the SalI, SphI and SacI sites of pCVD442; and pJMBL3 has the yscN and yscL fragments clones into the SalI, SphI and Sac I sites of pCVD442.

EXAMPLE 2

Secretion In Vitro

Experiments using cell culture assays were performed to determine whether Yops were secreted by chromosomally-encoded type III secretion systems. No evidence was found for Yop secretion in four in vitro assays, including YopJ-induced cytotoxity of RAW macrophages, phagocytosis of *Yersinia* by HeLa cells, YopH phosphastase activity in HeLa cells, and analysis of supernatants by SDS-PAGE from bacteria grown at 26° C. or 37° C. in high or low salt. However YopM was detected at comparable levels in cell lysates of wildtype (WT), yscB-L and yscN-U mutants grown at 37° C., and at much lower levels in the yscB-U, virFG mutant (FIG. 2).

EXAMPLE 3

In Vivo Characterization of Type III Secretion Deletions *Yersinia* Strains

Animal infection experiments were performed to assess the ability of *Yersinia* mutants to colonize tissues. Since rodents are a natural host for pathogenic *Yersinia* spp, these animals provide a good animal model.

Balb/C mice were orogastrically infected with $3\times10^8$ bacteria/mouse (10-fold greater than the $LD_{50}$) or $3\times10^9$ bacteria/mouse (100-fold greater than the $LD_{50}$). At each of the post-infection time points of 6 hours, 2 days and 5 days, mice were sacrificed and the following tissues were removed: spleen, mesenteric lymph nodes (MLN), Peyer's patches (PP), cecal lymph node (Clym), cecal lumen (Cin), cecal wall (Cwall), ileum lumen (SI in), ileal wall (SI wall), colonic lumen (LI in) and colonic walls (LI wall). Analyses performed on the tissues at each of the 6 hour, 2 day and 5 day post-infection time points indicate that the plasmid type III secretion system is important for GI tract colonization by day 2 (FIGS. 3-5). Of particular interest from the point of view of construction of a vector for delivery of a vaccine, are the data that show that colonization of the mesenteric lymph nodes (MLN) did not require presence of function of a pYV gene.

EXAMPLE 4

Failure of Orally Administered *Escherichia Coli* Cells to Colonize MLN

To determine whether any Gram-negative bacteria can survive in the MLN for 48 hours, mice were infected with a strain of *E. coli* that had been isolated from mice. After the passage of time, data from Balb/C mice infected with $3\times10^8$ bacteria/mouse and analyzed at 5 hours (FIG. 6) and 2 days (FIG. 7) indicated a lack of colonization of MLN at 2 days. *E. coli* cells were observed to be isolated from almost other all tissues tested at 5 hours, but were not observed in MLN at 2 days.

These data show that chromosomally encoded factors are important to colonize the MLN. Without being bound by any particular mechanism, a hypothesis to account for these data is that the reason *E. coli* infection was eliminated and the *Yersinia* remained because the animals had been previously exposed to an infection by cells of *E. coli*, and hence had become immunized.

To test this hypothesis, animals were infected with *Yersinia* and were then re-infected 3 weeks later with strains containing ysc deletions. At 5 days post-infection, the MLN of these animals were found to carry cells of only the strains having the ysc deletion.

EXAMPLE 5

Colonization of a Different Mouse Strain by *Yersinia*

The same experiment as in Example 3 however using a different mouse strain, C57BL/6, was performed. Animals were again infected with $3\times10^8$ bacteria/mouse, and tissues were analyzed for the presence of bacteria at a point in time 5 days post-infection.

The results obtained (FIG. 8) are comparable to those obtained using Balb/C mice. These data show that colonization of MLN by the plasmid type III secretion system is not an isolated phenomenon specific to a single host, and is generally true for animals from different strains.

EXAMPLE 6

Deletion Strains Compete with WT *Yersinia* to Colonize MLT

Results from competition infection of WT with yscN-L, yscB-L, yscB-U and pYV-showed that WT out-competed the plasmid-encoded type III secretion system mutants in the GI tract and Peyer's patches. However in the mesenteric lymph nodes the ysc mutants were found to compete successfully with WT.

These data show that chromosomally-encoded factors are involved in a *Yersinia* function to colonize the MLN, and that the pYV plasmid is important for *Yersinia* to survive in the GI tract.

EXAMPLE 7

Immunization of Mice with ysc Mutants and Protection Against WT

Because mutant strains were found to colonize the MLN and cause a modest pathogenesis, it was of practical interest to determine whether these strains would protect the host against a subsequent *Yersinia* WT infection.

Animals were administered $3\times10^{10}$ bacteria/mouse (a high dose which is 1000-fold greater than the number of bacteria corresponding to the dose that would be lethal to half of the recipients, if WT were administered, i.e., 1000-fold greater than the $LD_{50}$) of yscN-U, yscB-L, yscB-U and the strain lacking the virulence plasmid pYV-. The object of the analysis was to determine whether the animals could survive the high dose of the mutants, and if the animals as a result of infection would produce IgG which recognized the Yops, and would become resistant to the WT strain. As a pathogenesis marker, animal weight was recorded periodically, and the relative increase/lost weight percentage calculated. FIG. 9 shows that the average weight loss for the 6 mice infected with each ysc mutant strain. At 43 days post-infection, animals were re-infected with $3\times10^{9}$ bacteria/mouse of the WT strain, and were monitored for at least another 20 days.

The data show that all the animals survived the primary infection, and only one animal pre-infected with the pYV- strain died after WT infection. In contrast, a control group of "mock-infected" animals had a survival of only 1 of 6 animals following WT infection. The survival data are shown in Table 1.

TABLE 1

| Number of animals surviving infection with wildtype *Yersinia* after pre-infection with ysc mutant strains, as a fraction of total animals. | | | | |
|---|---|---|---|---|
| YscN-U | yscB-L | yscB-U | pYV- | Mock |
| 6/6 | 6/6 | 6/6 | 5/6 | 1/6 |

This study shows that the deletion strains and pYV- are not highly virulent when administered to animals by oro-gastrical infection; further, infection by these strains protects animals against a subsequent infection with the pathogenic WT strain.

EXAMPLE 8

Infection of Mice with a Low Dose of ysc Mutants

To determine whether an initial infection with a low dose might yield MLN colonization and protection against WT, animals were infected with $3\times10^{8}$ bacteria/mouse (10-fold greater than the $LD_{50}$). The secondary infection used $3\times10^{9}$ WT bacteria/mouse, as in the previous example.

TABLE 2

| Number of animals surviving infection with wildtype *Yersinia* after pre-infection with ysc mutant strains | | | | |
|---|---|---|---|---|
| YscN-U | yscB-L | yscB-U | P- | Mock |
| 5/5 | 4/5 | 4/5 | 4/5 | 1/5 |

The weight loss observed during the first infection was very mild. Further, protection against subsequent WT infection (Table 2) was again observed, although 1 out of 5 mice died in most of the pre-infected groups (FIG. 10).

EXAMPLE 9

Detection of Antibody Specific for Yops Following Infection

IgG against Yops could not be detected in most mice infected with the ysc mutants (there was one exception), and IgG against whole cell lysates of WT *Yersinia* was detected after four weeks.

TABLE 3

| Number of mice that have IgG to *Yersinia* Yops | | | | |
|---|---|---|---|---|
| yscN-U | YscB-L | yscB-U | VY | WT |
| 1/11 | 0/11 | 0/11 | 0/11 | 5/5 |

Thus, even though ysc mutant and pVY-mutant strains protect animals against subsequent infection with wildtype *Yersinia*, those infected with ysc mutants do not generate antibody to Yops.

EXAMPLE 10

Role of Chromosomal Type III Secretion System in Virulence

In order to determine the role of chromosomal type III system in colonization, a strain having a full deletion of genes spiA-ssaU was generated. Characterization of this strain showed that deletion of this system did not to affect bacterial growth or secretion of the Yops in culture under standard Yop-induction conditions i.e. 37C, low Ca2+.

These results indicate that the chromosomal type III secretion system does not play a role in colonization of the MLN. The chromosomal type III secretion system may be important for cecum and large intestine colonization at 2 days but not 5 days after infection (FIGS. 11-13).

EXAMPLE 11

In Vitro Yop Secretion in the spiA-ssaU Mutant and in the ysc Mutant Under Different Growth Conditions Expression of the plasmid encoded type III secretion system is best induced in vitro by low calcium medium and 37° C., whereas the chromosomal type III secretion system of *Y. enterocolitica* is induced at high salt (290 mM) and 26° C. Wildtype, yscN-U, spiA-ssaU, pYV- and double mutant strains were transformed with an isopropylthiogalactoside (IPTG) inducible plasmid that carries YopJ-FLAG or YopE-FLAG. Data on these mutants will determine the optimal genotype for secretion.

EXAMPLE 12

Further Attenuation of the Strain

Fukushima et al. (J. Clin. Micro. 1991) showed that a *Yersinia pseudotuberculosis* serotype IV lacking the virulence plasmid can cause acute Mesenteric Lymphadenitis in humans. While the ysc mutants of *Yersinia pseudotuberculosis* that are attenuated herein are a different serotype (type III) and failed to cause disease in the Examples herein in mice as determined by failure to cause weight loss, further attenuation is introduced into these strains in order to eliminate ability to produce disease in other non-rodent subjects such as agricultural animals, zoo animals, companion animals, and humans.

A gene for kasugamycin resistance (Mecsas et al., 2001, Inf 1 mm 67: 2779-2787) is introduced into the ysc mutants of *Yersinia pseudotuberculosis* and other *Yersinia* strains and Gram negative bacterial strains as disclosed herein, in order to slow growth and further attenuate pathogenicity.

These strains are used to infect and immunize subjects. Analyses of virulence, ability to colonize various tissues compared to the WT, and ability to confer immunity of the subjects compared to the WT and the ysc single mutant strains are performed as above. Further attenuation of the ysc in mutant immunizing strains is a desirable feature.

EXAMPLE 13

Attenuated *Erwinia* Strains for Crop Protection

The Gram negative bacterial plant pathogens *E. amylovora* and *E. carotovora* are responsible for substantial destruction of fruit and vegetable crops both during growth and during storage, particularly of organically grown crops. Occupation of the plant pathogenic environmental niche on the fruit and vegetable surfaces by a non-pathogenic mutant strain such as the ysc-like mutants as disclosed herein eliminates crop destruction during final ripening stages and subsequent storage of the crops.

What is claimed is:

1. An attenuated strain of a *Yersinia* bacterial species, the bacteria comprising an altered ysc gene such that the bacteria are attenuated wherein the altered ysc gene has a deletion, wherein the altered gene reduces secretion of *Yersinia* outer proteins (Yops) or reduces synthesis of Yops, and wherein the ysc gene deletion is selected from the group consisting of a deletion of at least one of: yscBL, yscNU, yscNU and virGF, and yscBL and yscNU.

2. The attenuated strain according to claim 1, wherein the altered gene reduces secretion of *Yersinia* outer proteins (Yops).

3. The attenuated strain according to claim 1, wherein the altered gene reduces synthesis of Yops.

4. The attenuated strain according to claim 1, wherein the altered gene eliminates secretion of Yops.

5. The attenuated strain according to claim 1, wherein the bacteria are a species selected from the group consisting of: *Y. pseudotuberculosis, Y pestis, Y enterocolitica*, and *Y ruckeri.*

6. The attenuated strain according to claim 3, wherein the ysc gene deletion is virGF.

7. The attenuated strain according to claim 1, in an effective dose.

8. The attenuated strain according to claim 7, wherein the dose is effective to provide to a subject immunity against infection with a wild type *Yersinia*.

9. The attenuated strain according to claim 8, wherein the wild type *Yersinia* is selected from the group consisting of *Y pseudoiuberculosis, Y pestis, Y ruckeri*, and *Y enterocolitica*.

10. The attenuated strain according to claim 8, wherein the effective dose provides immunity to at least about two orders of magnitude more wild type *Yersinia* bacteria compared to a level of immunity in a non-immunized subject.

11. The attenuated strain according to claim 8, wherein the effective dose provides immunity to at least about three orders of magnitude more wild type *Yersinia* bacteria compared to a level of immunity in a non-immunized subject.

12. The attenuated strain according to claim 8, wherein the effective dose provides immunity to at least about four orders of magnitude more wild type *Yersinia* bacteria compared to a level of immunity in a non-immunized subject.

13. The attenuated strain according to claim 8, wherein the effective dose comprises about $10^4$ to about $10^8$ bacteria per kg body weight of the subject.

14. The attenuated strain according to claim 8, wherein the effective dose comprises about $10^8$ to about $10^{12}$ bacteria per kg body weight of the subject.

15. The attenuated strain according to claim 8, wherein the subject is selected from the group of a mammal, a fish, and a bird.

16. The attenuated strain according to claim 8, wherein the subject is a human.

17. The attenuated strain according to claim 16, further comprising a gene conferring kasugamycin resistance.

18. The attenuated strain according to claim 15, wherein administering the strain to the mammal provides bacteria that persist in mesenteric lymph nodes of the mammal.

19. The attenuated strain according to claim 1, further comprising a recombinant gene.

20. The attenuated strain according to claim 19, wherein the recombinant gene encodes a desired gene product.

21. The attenuated strain according to claim 20, wherein the gene product is selected from the group consisting of an interferon, an erythropoietin, an enzyme, a growth factor, a leukokine, a chemokine, an antigen, a peptide hormone, and a precursor of any of these.

* * * * *

UNITED STATES PATENT AND TRADEMARK OFFICE

CERTIFICATE OF CORRECTION

PATENT NO. : 7,381,557 B2
APPLICATION NO. : 10/818071
DATED : June 3, 2008
INVENTOR(S) : Mecsas et al.

It is certified that error appears in the above-identified patent and that said Letters Patent is hereby corrected as shown below:

Claim 1, column 13, line 23: delete “ysc” and insert --*ysc*--

Claim 1, column 13, line 24: delete “ysc” and insert --*ysc*--

Claim 1, column 13, line 27: delete “ysc” and insert --*ysc*--

Claim 1, column 13, line 28: delete “yscBL” and insert --*yscBL*--

Claim 1, column 13, line 28: delete “yscNU” and insert --*yscNU*--

Claim 1, column 13, line 29: delete “yscNU and virGF” and insert --*yscNU* and *virGF*--

Claim 1, column 13, line 29: delete “yscBL and yscNU” and insert --*yscBL* and *yscNU*--

Claim 6, column 13, line 42: delete “virGF” and insert --*virGF*--

Claim 9, column 14, line 3: delete “*pseudoiuberculosis*” and insert --*pseudotuberculosis*--

Signed and Sealed this

Twenty-sixth Day of August, 2008

JON W. DUDAS
*Director of the United States Patent and Trademark Office*